US008198314B2

(12) United States Patent
Middlemiss et al.

(10) Patent No.: US 8,198,314 B2
(45) Date of Patent: *Jun. 12, 2012

(54) TREATMENT OF CRTH2-MEDIATED DISEASES AND CONDITIONS

(75) Inventors: David Middlemiss, Herts (GB); Mark Richard Ashton, Abingdon (GB); Edward Andrew Boyd, Abingdon (GB); Frederick Arthur Brookfield, Abingdon (GB); Michael George Hunter, Abingdon (GB); Mark Whittaker, Abingdon (GB); Chris Palmer, Abingdon (GB); Eric R. Pettipher, Abingdon (GB)

(73) Assignee: Oxagen Limited, Abingdon, Oxon (GB)

( * ) Notice: Subject to any disclaimer, the term of this patent is extended or adjusted under 35 U.S.C. 154(b) by 320 days.

This patent is subject to a terminal disclaimer.

(21) Appl. No.: 12/232,446

(22) Filed: Sep. 17, 2008

(65) Prior Publication Data

US 2009/0018138 A1 Jan. 15, 2009

Related U.S. Application Data

(63) Continuation of application No. 10/972,060, filed on Oct. 22, 2004, now Pat. No. 7,582,672.

(30) Foreign Application Priority Data

Oct. 23, 2003 (GB) .................... 0324763.2

(51) Int. Cl.
C07D 215/38 (2006.01)
A61K 31/04 (2006.01)
(52) U.S. Cl. .................. 514/415; 546/159; 546/294
(58) Field of Classification Search .............. 546/159, 546/494, 942; 514/415
See application file for complete search history.

(56) References Cited

U.S. PATENT DOCUMENTS

| 3,489,767 | A | 1/1970 | Yamamoto et al. |
| 3,557,142 | A | 1/1971 | Bell |
| 4,273,782 | A | 6/1981 | Cross et al. |
| 4,363,912 | A | 12/1982 | Cross et al. |
| 4,859,692 | A | 8/1989 | Bernstein et al. |
| 4,966,911 | A | 10/1990 | Clark et al. |
| 5,330,997 | A | 7/1994 | Mylari et al. |
| 6,214,991 | B1 | 4/2001 | Jones et al. |
| 6,426,344 | B2 * | 7/2002 | Jones et al. ............ 514/233.8 |
| 6,521,659 | B2 * | 2/2003 | Sredy et al. ............... 514/415 |
| 6,730,794 | B2 * | 5/2004 | Jones et al. ............... 548/159 |
| 6,964,980 | B2 * | 11/2005 | Sredy et al. ............... 514/415 |
| 7,105,514 | B2 * | 9/2006 | Jones et al. ............ 514/233.8 |
| 7,348,351 | B2 * | 3/2008 | Jennings et al. ........... 514/412 |
| 7,582,672 | B2 * | 9/2009 | Middlemiss et al. ...... 514/415 |
| 7,750,027 | B2 | 7/2010 | Armer et al. |
| 2003/0153751 | A1 | 8/2003 | Seehra et al. |
| 2004/0116488 | A1 | 6/2004 | Jennings et al. |
| 2005/0119268 | A1 | 6/2005 | Middlemiss et al. |
| 2007/0232681 | A1 | 10/2007 | Middlemiss et al. |
| 2009/0018139 | A1 | 1/2009 | Middlemiss et al. |
| 2009/0018338 | A1 | 1/2009 | Middlemiss et al. |
| 2009/0023788 | A1 * | 1/2009 | Middlemiss et al. ......... 514/367 |
| 2009/0186923 | A1 | 7/2009 | Armer et al. |
| 2009/0192195 | A1 | 7/2009 | Armer et al. |
| 2010/0022613 | A1 | 1/2010 | Armer et al. |
| 2010/0035956 | A1 | 2/2010 | Armer et al. |
| 2010/0041699 | A1 | 2/2010 | Boyd et al. |
| 2010/0056544 | A1 | 3/2010 | Lovell |
| 2010/0063103 | A1 | 3/2010 | Armer et al. |
| 2010/0266535 | A1 | 10/2010 | Armer et al. |
| 2010/0330077 | A1 | 12/2010 | Armer et al. |

FOREIGN PATENT DOCUMENTS

| EP | 0 054 417 B1 | 6/1982 |
| EP | 0 539 117 A1 | 4/1993 |
| EP | 0 574 174 A3 | 12/1993 |
| EP | 0 851 030 A1 | 7/1998 |
| EP | 1 170 594 A2 | 1/2002 |
| EP | 1 211 513 B1 | 1/2006 |
| GB | 1 356 834 | 6/1974 |
| GB | 1 407 658 | 9/1975 |
| GB | 1 460 348 | 1/1977 |
| JP | 43-24418 | 4/1966 |
| JP | 2001-247570 A | 9/2001 |
| PL | 65781 | 10/1972 |
| WO | WO 93/12786 A1 | 7/1993 |
| WO | WO 95/06046 A1 | 3/1995 |
| WO | WO 9603376 A1 | 2/1996 |
| WO | WO 96/26207 A1 | 8/1996 |
| WO | WO 99/43651 A2 | 9/1999 |
| WO | WO 99/50268 A2 | 10/1999 |
| WO | WO 00/32180 A2 | 6/2000 |
| WO | 0151489 * | 7/2001 |
| WO | WO 01/51489 A2 | 7/2001 |
| WO | WO 01/64205 A2 | 9/2001 |
| WO | WO 03/066046 A1 | 8/2003 |
| WO | WO 03/066047 A1 | 8/2003 |
| WO | WO 03/097042 A1 | 11/2003 |
| WO | WO 03/097598 A1 | 11/2003 |
| WO | WO 03/101961 A1 | 12/2003 |
| WO | WO 03/101981 A1 | 12/2003 |
| WO | WO 2004/058164 A2 | 7/2004 |

OTHER PUBLICATIONS

Matassa, J Med CHem, vol. 33, pp. 1781-1790, 1990.*
Murray, J. J. et al., "Release of Prostaglandin $D_2$ into Human Airways During Acute Antigen Challenge," *N. Engl. J. Med.* 315:800-804, The Massachusetts Medical Society, Boston, MA 02115 (1986).
Sampson, S. E. et al., "Effect of Inhaled Prostaglandin $D_2$ in Normal and Atopic Subjects, and of Pretreatment with Leukotriene $D_4$," *Throax* 52:513-518, BMJ Publishing Group, London (1997).
Dialog File 351, Accession No. 161699, Derwent WPI English language abstract for JP 43-24418, 1966.
UK Search Report for UK Application No. GB 0324763.2, mailed Feb. 27, 2004, New Port, UK.
European Search Report for European File No. RS 111022 GB, mailed May 11, 2004, Rijswijk, The Netherlands.

(Continued)

*Primary Examiner* — D M Seaman
(74) *Attorney, Agent, or Firm* — Sterne, Kessler, Goldstein & Fox P.L.L.C.

(57) ABSTRACT

The present invention provides indole derivatives that antagonize prostaglandin $D_2$, and that can be used to treat inflammatory diseases mediated by prostaglandin $D_2$.

17 Claims, No Drawings

OTHER PUBLICATIONS

Unpublished U.S. Appl. No. 12/779,638, filed May 13, 2010; inventors: Hunter et al., U.S. Patent and Trademark Office, Alexandria, Virginia.

Unpublished U.S. Appl. No. 13/014,314, filed Jan. 26, 2011; inventors: Amer et al., U.S. Patent and Trademark Office, Alexandria, Virginia.

Unpublished U.S. Appl. No. 13/017,860, filed Jan. 31, 2011; inventors: Armer et al., U.S. Patent and Trademark Office, Alexandria, Virginia.

Office Action mailed Jun. 21, 2007, in U.S. Appl. No. 10/972,060, to Middlemiss, D., et al., U.S. Patent and Trademark Office, Alexandria, Virginia.

Office Action mailed Feb. 7, 2008, in U.S. Appl. No. 10/972,060, to Middlemiss, D., et al., U.S. Patent and Trademark Office, Alexandria, Virginia.

Office Action mailed Oct. 1, 2010, in U.S. Appl. No. 12/232,444, to Middlemiss, D., et al., U.S. Patent and Trademark Office, Alexandria, Virginia.

Office Action mailed Oct. 4, 2010, in U.S. Appl. No. 12/232,447, to Middlemiss, D., et al., U.S. Patent and Trademark Office, Alexandria, Virginia.

Office Action mailed Oct. 1, 2010, in U.S. Appl. No. 12/232,445, to Middlemiss, D., et al., U.S. Patent and Trademark Office, Alexandria, Virginia.

Cross, P. E. et al., "Selective Thromboxane Synthetase Inhibitors, 2. 3-(1*H*-Imidazol-1-ylmethyl)-2-methyl-1*H*-indole-1-propanoic Acid and Analogues," *J. Med. Chem.* 29:342-346, American Chemical Society, Washington, DC (1986).

Emery, D. L. et al., "Prostaglandin $D_2$ causes accumulation of eosinophils in the lumen of the dog trachea," *J. Appl. Physiol.* 67:959-962, The American Physiological Society, Bethesda, MD, (1989).

Fujitani, Y. et al., "Pronounced Eosinophilic Lung Inflammation and Th2 Cytokine Release in Human Lipocalin-Type Prostaglandin D Synthase Transgenic Mice," *J. Immunol.* 168:443-449, The American Association of Immunologists, Bethesda, Maryland, (2002).

Gervais, F. G. et al., "Selective modulation of chemokinesis, degranulation, and apoptosis in eosinophils through the $PGD_2$ receptors CRTH2 and DP," *The J. Allergy Clin. Immunol.* 108:982-988, Mosby, St Louis, MO, (2001).

Hardy, C. C. et al., "The Bronchoconstrictor Effect of Inhaled Prostaglandin $D_2$ in Normal and Asthmatic Men," *N. Engl. J. Med.* 311:209-213, The Massachusetts Medical Society, Boston, MA (1984).

Hirai, H. et al., "Prostaglandin D2 Selectively Induces Chemotaxis in T Helper Type 2 Cells, Eosinophils, and Basophils via Seven-Transmembrane Receptor CRTH2," *J. Exp. Med.* 193:255-261,The Rockefeller University Press, New York, NY (2001).

Kumar, S., et al., "Novel Indium-Mediated Ternary Reactions Between Indole-3-Carboxaldehydes-Allyl Bromide-Enamines: Facile Synthesis of Bisindolyl-and Indolyl-Heterocyclic Alkanes," *Tet. Lett.* 44:2101-2104, Elsevier Science Ltd., London (Jan. 2003).

Matassa, V. G. et al., "Evolution of a Series of Peptidoleukotriene Antagonists: Synthesis and Structure/Activity Relationships of 1,3,5-Substituted Indoles and Indazoles," *J. Med. Chem.* 33:1781-1790, American Chemical Society, Washington, DC (1990).

Menciu, C., et al., "New *N*-(Pyridin-4-yl)-(indol-3-yl)acetamides and Propanamides as Antiallergic Agents," *J. Med. Chem.* 42:638-648, American Chemical Society, Washington, DC (1999).

Monneret, G. et al., "15R-Methyl-Prostaglandin D2 is a Potent and Selective CRTH2/DP2 Receptor Agonist in Human Eosinophils," *J. Pharmacol. Exp. Ther.* 304:349-355, The American Society of Pharmacology and Experimental Therapeutics, Bethesda, MD (Jan. 2003).

\* cited by examiner

TREATMENT OF CRTH2-MEDIATED DISEASES AND CONDITIONS

This application is a continuation of U.S. application Ser. No. 10/972,060, filed Oct. 22, 2004, which claims the benefit of Great Britain Patent Application No. 0324763.2, filed Oct. 23, 2003. The entirety of each of these applications is incorporated by reference herein.

FIELD OF THE INVENTION

The present invention relates to indole derivatives that antagonize prostaglandin $D_2$, and that can be used to treat inflammatory diseases mediated by prostaglandin $D_2$.

BACKGROUND OF THE INVENTION

The present invention relates to the use of certain compounds in the treatment and prevention of allergic diseases such as asthma, allergic rhinitis and atopic dermatitis and other inflammatory diseases mediated by prostaglandin $D_2$ ($PGD_2$) acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al, (1986), *N. Engl. J. Med* 315:800-804). Instillation of $PGD_2$ into airways can provoke many features of the asthmatic response including bronchoconstriction (Hardy et al, (1984)*N. Engl. J. Med* 311:209-213; Sampson et al, (1997) *Thorax* 52:513-518) and eosinophil accumulation (Emery et al, (1989) *J. Appl. Physiol.* 67:959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al, (2002) *J. Immunol.* 168:443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al, (2001) *J. Exp. Med.* 193:255-261, and EP0851030 and EP-A-1211513 and Bauer et al, EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al, 2001; Monneret et al, (2003) *J. Pharmacol. Exp. Ther.* 304:349-355). In contrast, the selective DP agonist BW245C does not promote migration of Th2 lymphocytes or eosinophils (Hirai et al, 2001; Gervais et al, (2001) *J. Allergy Clin. Immunol.* 108:982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune disease, reperfusion injury and a number of inflammatory conditions, all of which are mediated by the action of $PGD_2$ at the CRTH2 receptor.

Compounds which bind to CRTH2 are taught in WO-A-03066046 and WO-A-03066047. These compounds are not new but were first disclosed, along with similar compounds, in GB 1356834, GB 1407658 and GB 1460348, where they were said to have anti-inflammatory, analgesic and anti-pyretic activity. WO-A-03066046 and WO-A-03066047 teach that the compounds to which they relate are modulators of CRTH2 receptor activity and are therefore of use in the treatment or prevention of obstructive airway diseases such as asthma, chronic obstructive pulmonary disease (COPD) and a number of other diseases including various conditions of bones and joints, skin and eyes, GI tract, central and peripheral nervous system and other tissues as well as allograft rejection.

PL 65781 and JP 43-24418 also relate to indole derivatives which are similar in structure to indomethacin and, like indomethacin, are said to have anti-inflammatory and anti-pyretic activity. Thus, although this may not have been appreciated at the time when these documents were published, the compounds they describe are COX inhibitors, an activity which is quite different from that of the compounds of the present invention. Indeed, COX inhibitors are contraindicated in the treatment of many of the diseases and conditions, for example asthma and inflammatory bowel disease for which the compounds of the present invention are useful, although they may sometimes be used to treat arthritic conditions.

We have now discovered that certain indole derivatives in which the indole nitrogen is substituted with a carboxylic acid moiety are antagonists of $PGD_2$ at the CRTH2 receptor and are useful in a method for the treatment of diseases and conditions mediated by $PGD_2$ at the CRTH2 receptor, the method comprising administering to a patient in need of such treatment a suitable amount of one of the compounds.

SUMMARY OF THE INVENTION

In one aspect the invention provides compounds of general formula (I):

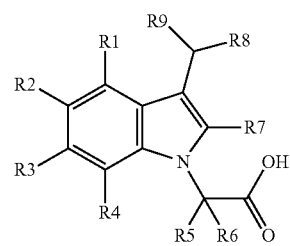

wherein $R^1$, $R^2$, $R^3$ and $R^4$ are independently hydrogen, halo, $C_1$-$C_6$ alkyl, —O($C_1$-$C_6$ alkyl), —CON($R^{11}$)$_2$, —SOR$^{11}$, —SO$_2$R$^{11}$, —SO$_2$N($R^{11}$)$_2$, —N($R^{11}$)$_2$, —NR$^{11}$COR$^{11}$, —CO$_2$R$^{11}$, —COR$^{11}$, —SR$^{11}$, —OH, —NO$_2$ or —CN;

each $R^{11}$ is independently hydrogen or $C_1$-$C_6$ alkyl;

$R^5$ and $R^6$ are each independently hydrogen, or $C_1$-$C_6$ alkyl or together with the carbon atom to which they are attached form a $C_3$-$C_7$ cycloalkyl group;

$R^7$ is hydrogen or $C_1$-$C_6$ alkyl;

$R^8$ is an aromatic moiety optionally substituted with one or more substituents selected from halo, $C_1$-$C_6$ alkyl, —O($C_1$-$C_6$)alkyl, —CON($R^{11}$)$_2$, —SOR$^{11}$, —SO$_2$R$^{11}$, —SO$_2$N($R^{11}$)$_2$, —N($R^{11}$)$_2$, —NR$^{11}$COR$^{11}$, —CO$_2$R$^{11}$, —COR$^{11}$, —SR$^{11}$, —OH, —NO$_2$ or —CN;

wherein $R^{11}$ is as defined above;

$R^9$ is hydrogen, or $C_1$-$C_6$ alkyl;

provided that:

$R^8$ is not phenyl substituted with —COOH;

when any two of $R^1$, $R^2$, $R^3$ and $R^4$ are hydrogen, neither of the other two of $R^1$, $R^2$, $R^3$ and $R^4$ is $C_3$-$C_6$ alkyl;

or a pharmaceutically acceptable salt, hydrate, solvate, complex or prodrug thereof;

wherein the compounds are useful for the treatment or prevention of allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis and also other PGD$_2$-mediated diseases, for example autoimmune diseases such as hyper IgE syndrome and systemic lupus erythematosus, psoriasis, acne, multiple sclerosis, allograft rejection, reperfusion injury, chronic obstructive pulmonary disease, as well as, in some cases, rheumatoid arthritis, psoriatic arthritis and osteoarthritis.

A second aspect of the invention provides compounds of a general formula (II):

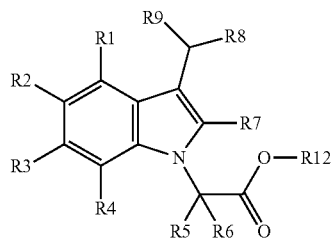

II wherein $R^1$, $R^2$, $R^3$, $R^4$, $R^5$, $R^6$, $R^7$, $R^8$ and $R^9$ are as defined for general formula (I); $R^{12}$ is $C_1$-$C_6$ alkyl, aryl, (CH$_2$)$_m$OC(=O)$C_1$-$C_6$alkyl, (CH$_2$)$_m$N($R^{13}$)$_2$, CH((CH$_2$)$_m$O(C=O)$R^{14}$)$_2$;

m is 1 or 2;

$R^{13}$ is hydrogen or methyl;

$R^{14}$ is $C_1$-$C_{18}$ alkyl;

wherein compounds of formula (II) are useful for the treatment or prevention of PGD$_2$-mediated diseases.

A third aspect of the invention provides methods for the treatment or prevention of PGD$_2$-mediated diseases, the methods comprising administering an effective amount of one or more compounds of general formulas (I) or (II) to a subject in need thereof.

DETAILED DESCRIPTION OF THE PREFERRED EMBODIMENT

Therefore, in a first aspect of the invention, there is provided the use of a compound of general formula (I):

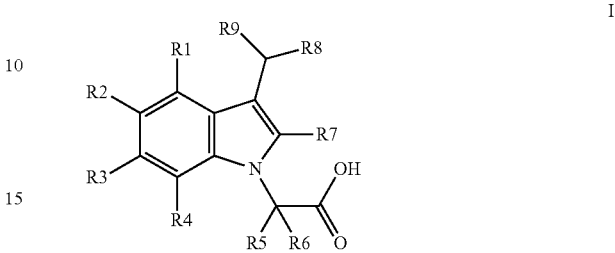

I wherein $R^1$, $R^2$, $R^3$ and $R^4$ are independently hydrogen, halo, $C_1$-$C_6$ alkyl, —O($C_1$-$C_6$ alkyl), —CON($R^{11}$)$_2$, —SOR$^{11}$, —SO$_2$R$^{11}$, —SO$_2$N($R^{11}$)$_2$, —N($R^{11}$)$_2$, —NR$^{11}$COR$^{11}$, —CO$_2$R$^{11}$, —COR$^{11}$, —SR$^{11}$, —OH, —NO$_2$ or —CN;

each $R^{11}$ is independently hydrogen or $C_1$-$C_6$ alkyl;

$R^5$ and $R^6$ are each independently hydrogen, or $C_1$-$C_6$ alkyl or together with the carbon atom to which they are attached form a $C_3$-$C_7$ cycloalkyl group;

$R^7$ is hydrogen or $C_1$-$C_6$ alkyl;

$R^8$ is an aromatic moiety optionally substituted with one or more substituents selected from halo, $C_1$-$C_6$ alkyl, —O($C_1$-$C_6$)alkyl, —CON($R^{11}$)$_2$, —SOR$^{11}$, —SO$_2$R$^{11}$, —SO$_2$N($R^{11}$)$_2$, —N($R^{11}$)$_2$, —NR$^{11}$COR$^{11}$, —CO$_2$R$^{11}$, —COR$^{11}$, —SR$^{11}$, —OH, —NO$_2$ or —CN;

wherein $R^{11}$ is as defined above;

$R^9$ is hydrogen, or $C_1$-$C_6$ alkyl;

provided that:

$R^8$ is not phenyl substituted with —COOH;

when any two of $R^1$, $R^2$, $R^3$ and $R^4$ are hydrogen, neither of the other two of $R^1$, $R^2$, $R^3$ and $R^4$ is $C_3$-$C_6$ alkyl;

or a pharmaceutically acceptable salt, hydrate, solvate, complex or prodrug thereof;

wherein the compounds are useful for the treatment or prevention of allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis and also other PGD$_2$-mediated diseases, for example autoimmune diseases such as hyper IgE syndrome and systemic lupus erythematosus, psoriasis, acne, multiple sclerosis, allograft rejection, reperfusion injury, chronic obstructive pulmonary disease, as well as, in some cases, rheumatoid arthritis, psoriatic arthritis and osteoarthritis.

WO-A-9950268, WO-A-0032180, WO-A-0151849 and WO-A-0164205 all relate to compounds which are similar to the compounds of general formula (I). However, these compounds are said to be aldose reductase inhibitors useful in the treatment of diabetes mellitus (WO-A-9950268, WO-A-0032180 and WO-A-0164205) or hypouricemic agents (WO-A-0151849). There is no suggestion in any of these documents that the compounds would be useful for the treatment of diseases and conditions mediated by PGD$_2$ at the CRTH2 receptor. The preferred compounds described in these prior art documents mostly have a benzothiazole substituent in the position equivalent to $R^8$ of general formula (I).

U.S. Pat. No. 4,363,912 relates to compounds similar to those of the present invention which are said to be inhibitors of thromboxane synthetase and to be useful in the treatment of conditions such as thrombosis, ischaemic heart disease and stroke. The compounds have a pyridyl group in the position equivalent to $R^8$ of general formula (I).

WO-A-9603376 relates to compounds which are said to be sPLA$_2$ inhibitors which are useful in the treatment of bronchial asthma and allergic rhinitis. These compounds all have amide or hydrazide substituents in place of the carboxylic acid derivative of the compounds of the present invention.

JP 2001247570 relates to a method of producing a 3-benzothiazolylmethyl indole acetic acid, which is said to be an aldose reductase inhibitor.

U.S. Pat. No. 4,859,692 relates to compounds which are said to be leukotriene antagonists useful in the treatment of conditions such as asthma, hay fever and allergic rhinitis as well as certain inflammatory conditions such as bronchitis, atopic and ectopic eczema. The compounds of this document are similar to the compounds of general formula (I), but general formula (I) specifically excludes compounds in which $R^8$ is phenyl substituted with a —COOH group, which is the only area of overlap. Furthermore, *J. Med. Chem.*, 6(33):1781-1790 (1990), which has the same authors as this prior patent application, teaches that compounds with an acetic acid group on the indole nitrogen do not have significant peptidoleukotriene activity. In view of this, it is most surprising that the compounds of the present invention, which all have an acetic acid group on the indole nitrogen, are useful for treating conditions such as asthma, hay fever and allergic rhinitis.

U.S. Pat. No. 4,273,782 is directed to compounds similar to those of general formula (I), which are said to be useful in the treatment of conditions such as thrombosis, ischaemic heart disease, stroke, transient ischaemic attack, migraine and the vascular complications of diabetes. There is no mention in the document of conditions mediated by the action of PGD$_2$ at the CRTH2 receptor. The compounds of this prior art document all have an imidazole group in the position equivalent to $R^8$ of general formula (I).

U.S. Pat. No. 3,557,142 relates to 3-substituted-1-indole carboxylic acids and esters which are said to be useful in the treatment of inflammatory conditions.

WO-A-03/097598 relates to compounds which are CRTH2 receptor antagonists. They do not have an aromatic substituent in the position equivalent to $R^8$ of general formula (I).

Cross et al, *J. Med. Chem.* 29:342-346 (1986) relates to a process for preparing compounds similar to those of general formula (I) from the corresponding esters similar to the compounds of general formula (II). The compounds to which it relates are said to be inhibitors of thromboxane synthetase and all have an imidazole group in the position equivalent to $R^8$ of general formula (I).

EP-A-0539117 relates to leukotriene antagonists which are similar in structure to the compounds of general formula (I).

US 2003/0153751 relates to compounds which are sPLA$_2$ inhibitors. Although the structural formula covers compounds similar to those of general formula (I), all of the exemplified compounds have bulky substituents at the 2- and 5-positions of the indole system and are therefore very different from the compounds of the present invention.

US 2004/011648 discloses compounds which are similar to the compounds of general formula (I) and which are inhibitors of PAI-1. There is no suggestion that the compounds might have CRTH2 antagonist activity.

WO 2004/058164 relates to compounds which are said to be asthma and allergic inflammation modulators. The only compounds for which activity is demonstrated are entirely different in structure from the compounds of general formula (I).

Compounds which bind to the CRTH2 receptor are disclosed in WO-A-03/097042 and WO-A-03/097598. These compounds are indole acetic acids but in WO-A-03/097042 the indole system is fused at the 2-3 positions to a 5-7 membered carbocyclic ring. In WO-A-03/097598 there is a pyrrolidine group at the indole 3-position.

WO-A-03/101981 and WO-A-03/101961 both relate to compound which are said to be CRTH2 antagonists but which differ in structure from the compounds of general formula (I) because there is an —S— or —SO$_2$— group linked to the indole 3-position in place of the CH$_2$ group of the compounds of general formula (I).

In the present specification "C$_1$-C$_6$ alkyl" refers to a straight or branched saturated hydrocarbon chain having one to six carbon atoms and optionally substituted with one or more halo substituents or with one or more C$_3$-C$_7$ cycloalkyl groups. Examples include methyl, ethyl, n-propyl, isopropyl, t-butyl, n-hexyl, trifluoromethyl, 2-chloroethyl, methylenecyclopropyl, methylenecyclobutyl and methylenecyclopentyl.

"C$_1$-C$_4$ alkyl" and "C$_1$-C$_{18}$ alkyl" have similar meanings except that they contain from one to four and from one to eighteen carbon atoms respectively.

C$_3$-C$_7$ cycloalkyl refers to a saturated 3 to 7 membered carbocyclic ring. Examples of such groups include cyclopropyl, cyclobutyl, cyclopentyl and cyclohexyl.

In the present specification, "halo" refers to fluoro, chloro, bromo or iodo.

The terms "aromatic moiety" and "aryl" in the context of the present specification refer to an aromatic ring system having from 5 to 14 ring carbon atoms and containing up to three rings, one or more of which may be replaced by a nitrogen, oxygen or sulfur atom. Examples of aromatic moieties are benzene, pyridine, naphthalene, biphenyl, quinoline, isoquinoline, quinazoline, thiazole, benzthiazole, benzoxazole, benzimidazole, indole, indazole and imidazole ring systems.

Appropriate pharmaceutically and veterinarily acceptable salts of the compounds of general formulae (I) and (II) include basic addition salts such as sodium, potassium, calcium, aluminium, zinc, magnesium and other metal salts as well as choline, diethanolamine, ethanolamine, ethyl diamine and other well known basic addition salts.

Where appropriate, pharmaceutically or veterinarily acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts which are not pharmaceutically or veterinarily acceptable may still be valuable as intermediates.

Prodrugs are any covalently bonded compounds which release the active parent drug according to general formula (I)

in vivo. Examples of prodrugs include alkyl esters of the compounds of general formula (I), for example the esters of general formula (II) below.

If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

In the compounds of general formula (I), it is preferred that, independently or in any combination:
$R^1$ is halo or hydrogen;
$R^2$ is halo or hydrogen;
$R^3$ is halo or hydrogen;
$R^4$ is halo or hydrogen.

In more preferred compounds, $R^1$, $R^3$ and $R^4$ are hydrogen, while $R^2$ is halo, particularly fluoro.

In preferred compounds of general formula (I), $R^5$ and $R^6$ are each independently hydrogen or $C_1$-$C_4$ alkyl. However, in more active compounds, at least one, and preferably both of $R^5$ and $R^6$ are hydrogen.

Similarly, it is preferred that $R^9$ is hydrogen or $C_1$-$C_4$ alkyl, most preferably hydrogen.

Compounds of general formula (I) preferably have an $R^7$ group chosen from H or $C_1$-$C_6$ alkyl; most suitably $R^7$ is methyl.

In preferred compounds of general formula (I), $R^8$ is phenyl, naphthalenyl, quinolinyl, quinoxalinyl, thiazolyl, biphenyl or benzothiazolyl, any of which may optionally be substituted with one or more substituents as defined above.

In particular, it is preferred that $R^8$ is phenyl substituted at the 4-position or naphthalen-2-yl, quinolin-2-yl, quinoxalin-2-yl, thiazol-2-yl or berizothiazol-2-yl, any of which may optionally be substituted with one or more of the substituents defined above.

When the $R^8$ moiety is substituted, preferred substitutents include halo, $C_1$-$C_4$ alkyl, $C_1$-$C_4$ haloalkyl, $C_1$-$C_4$ alkoxy, $C_1$-$C_4$ alkylsulfonyl and hydroxy.

Especially preferred substituents for the $R^8$ moiety include chloro, fluoro, methyl, ethyl, t-butyl, trifluoromethyl, methoxy, methanesulfonyl and hydroxy.

Among the most preferred compounds are the following:
1. {3-[1-(4-Chloro-phenyl)-ethyl]-5-fluoro-2-methyl-indol-1-yl}-acetic acid;
2. {(5-Fluoro-2-methyl-3-[1 (4-trifluoromethyl-phenyl)-ethyl]-indol-1-yl}-acetic acid;
3. {(3-[1-(4-tert-Butyl-phenyl)-ethyl]-5-fluoro-2-methyl-indol-1-yl)}-acetic acid;
4. {5-Fluoro-3-[1-(4-methanesulfonyl-phenyl)-ethyl]-2-methyl-indol-1-yl}-acetic acid;
5. [5-Fluoro-2-methyl-3-(1-naphthalen-2-yl-ethyl)-indol-1-yl]-acetic acid;
6. (5-Fluoro-2-methyl-3-quinolin-2-ylmethyl-indol-1-yl)-acetic acid;
7. (5-Fluoro-2-methyl-3-naphthalen-2-ylmethyl-indol-1-yl)-acetic acid;
8. [5-Fluoro-3-(8-hydroxy-quinolin-2-ylmethyl)-2-methyl-indol-1-yl]-acetic acid;
9. (5-Fluoro-2-methyl-3-quinoxalin-2-ylmethyl-indol-1-yl)-acetic acid;
10. [5-Fluoro-3-(4-methoxy-benzyl)-2-methyl-indol-1-yl]-acetic acid;
11. (5-Fluoro-2-methyl-3-thiazol-2-ylmethyl-indol-1-yl)-acetic acid ethyl ester;
12. [3-(4-Chloro-benzyl)-5-fluoro-2-methyl-indol-1-yl]-acetic acid;
13. (3-Benzothiazol-2-ylmethyl-5-fluoro-2-methyl-indol-1-yl)-acetic acid;
14. [5-Fluoro-2-methyl-3-(4-trifluoromethyl-benzyl)-indol-1-yl]-acetic acid;
15. [5-Fluoro-2-methyl-3-(4-tert-butyl-benzyl)-indol-1-yl]-acetic acid;
16. (3-Biphenyl-4-ylmethyl-5-fluoro-2-methyl-indol-1-yl)-acetic acid;
17. [5-Fluoro-3-(4-methanesulfonyl-benzyl)-2-methyl-indol-1-yl]-acetic acid;
18. [5-Fluoro-3-(6-fluoro-quinolin-2-ylmethyl)-2-methyl-indol-1-yl]-acetic acid;
19. (±)-3-(1-Benzothiazol-2-yl-ethyl)-5-fluoro-2-methyl-indol-1-yl)-acetic acid;
20. [3-(4,5,7-Trifluoro-benzothiazol-2-ylmethyl)-indol-1-yl]-acetic acid (lidorestat);
21. (2-Methyl-3-quinolin-2-ylmethyl-indol-1-yl)-acetic acid;
22. (5-Chloro-2-methyl-3-quinolin-2-ylmethyl-indol-1-yl)-acetic acid;

or the $C_1$-$C_6$ alkyl, aryl, $(CH_2)_mOC(\!=\!O)C_1$-$C_6$alkyl, $(CH_2)_mN(R^{13})_2$, $CH((CH_2)_mO(C\!=\!O)R^{14})_2$ esters of any of the above; wherein m is 1 or 2;
$R^{13}$ is hydrogen or methyl;
$R^{14}$ is $C_1$-$C_{18}$ alkyl.

Although some compounds of general formula (I) are known from the prior art, others represent a novel selection since they are not exemplified and the aromatic groups in the $R^8$ position are not said to be preferred. Furthermore, these compounds have, surprisingly, been shown by the present inventors to have activity as antagonists of $PGD_2$ at the CRTH2 receptor.

Therefore, in a further aspect of the invention there is provided a compound of general formula (I) wherein $R^1$, $R^2$, $R^3$, $R^4$, $R^5$, $R^6$, $R^7$ and $R^9$ are as defined above and $R^8$ is a phenyl, naphthalenyl, thiazole, biphenyl, quinolinyl or quinoxalinyl group, any of which may be substituted with one or more halo, $C_1$-$C_6$ alkyl, —O($C_1$-$C_6$)alkyl, —$SO_2R^{11}$ or —OH groups;

provided that.

$R^8$ is not unsubstituted phenyl or phenyl substituted with —COOH;

when any two of $R^1$, $R^2$, $R^3$ and $R^4$ are hydrogen, neither of the other two of $R^1$, $R^2$, $R^3$ and $R^4$ is $C_3$-$C_6$ alkyl;

when all of $R^1$, $R^2$, $R^3$ and $R^4$ are hydrogen, $R^8$ is not 4-chlorophenyl.

In these novel compounds, preferred $R^8$ groups are is phenyl substituted at the 4-position, naphthalen-2-yl, quinolin-2-yl, quinoxalin-2-yl or thiazol-2-yl and preferred substituents for these groups are chloro, fluoro, methyl, ethyl, t-butyl, trifluoromethyl, methoxy, methanesulfonyl and hydroxy.

Preferred $R^1$, $R^2$, $R^3$, $R^4$, $R^5$, $R^6$, $R^7$ and $R^9$ groups are as specified above.

Among the most preferred novel compounds are Compounds 1 to 19, 21 and 22 listed above and these compounds form a further aspect of the invention. Compound 20 was disclosed in WO-A-9950268.

The compound of general formula (I) may be derived in vivo from a prodrug. The prodrug may be a compound of general formula (II):

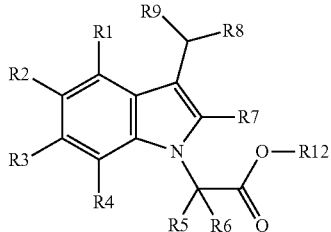

wherein $R^1$, $R^2$, $R^3$, $R^4$, $R^5$, $R^6$, $R^7$, $R^8$ and $R^9$ are as defined for general formula (I); $R^{12}$ is $C_1$-$C_6$ alkyl, aryl, $(CH_2)_mOC(=O)C_1$-$C_6$alkyl, $(CH_2)_mN(R^{13})_2$, $CH((CH_2)_mO(C=O)R^{14})_2$;

m is 1 or 2;

$R^{13}$ is hydrogen or methyl;

$R^{14}$ is $C_1$-$C_{18}$ alkyl.

Therefore, in a further aspect of the invention there is provided the use of a compound of general formula (II) as defined above in the preparation of an agent for the treatment or prevention of diseases and conditions mediated by $PGD_2$ at the CRTH2 receptor.

Examples of particularly suitable $R^{12}$ groups when the compound of general formula (II) is used as a prodrug include:

methyl, ethyl, propyl, phenyl, $CH_2OC(=O)tBu$, $CH_2CH_2N(Me)_2$, $CH_2CH_2NH_2$ or $CH(CH_2O(C=O)R^{14})_2$ wherein $R^{14}$ is as defined above.

Compounds of general formula (II) wherein $R^8$ is a phenyl, naphthalenyl, biphenyl, quinolyl or quinoxalyl group, any of which may be substituted with one or more halo, $C_1$-$C_6$ alkyl, —$O(C_1$-$C_6)$alkyl, —$SO_2R^{11}$ or —OH groups;

provided that $R^8$ is not unsubstituted phenyl or phenyl substituted with —COOH;

when any two of $R^1$, $R^2$, $R^3$ and $R^4$ are hydrogen, neither of the other two of $R^1$, $R^2$, $R^3$ and $R^4$ is $C_3$-$C_6$ alkyl;

when all of $R^1$, $R^2$, $R^3$ and $R^4$ are hydrogen, $R^8$ is not 4-chlorophenyl;

are new.

Some of the most preferred compounds of general formula (II) are the $C_1$-$C_6$ alkyl, aryl, $(CH_2)_mOC(=O)C_1$-$C_6$alkyl, $(CH_2)_mN(R^{13})_2$, $CH((CH_2)_mO(C=O)R^{14})_2$ esters of Compounds 1 to 19 above, wherein m, $R^{13}$ and $R^{14}$ are as defined above.

When the compound of general formula (II) acts as a prodrug, it is later transformed to the drug by the action of an esterase in the blood or in a tissue of the patient.

As is described in WO-A-9950268, compounds of general formula (I) may be prepared from compounds of general formula (II) in which $R^{12}$ is $C_1$-$C_6$ alkyl by hydrolysis with an alkali such as sodium or lithium hydroxide. The reaction may take place in an aqueous solvent or an organic solvent or a mixture of the two. A typical solvent used for the reaction is a mixture of tetrahydrofuran and water.

Compounds of general formula (II) may be prepared from compounds of general formula (III):

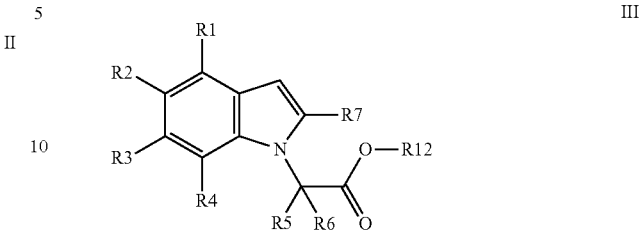

wherein $R^1$, $R^2$, $R^3$, $R^4$, $R^5$, $R^6$ and $R^7$ are as defined in general formula (I) and $R^{12}$ is as defined in general formula (II); by reaction with a compound of general formula (IV):

$$R^9C(=O)R^8 \qquad (IV)$$

wherein $R^9$ is as defined for general formula (I);

under acidic reductive alkylation conditions. Compounds of general formulae (III) and (IV) are readily available or can be prepared by methods well known to those skilled in the art.

Other methods of preparing compounds of general formulae (I) and (II) are set out in WO-A-9950268 and WO-A-0151489.

Compounds of general formula (I) are antagonists of $PGD_2$ at the CRTH2 receptor and compounds of general formula (II) are prodrugs for compounds of general formula (I). Compounds of general formulae (I) and (II) are therefore useful in a method for the treatment of diseases and conditions mediated by $PGD_2$ at the CRTH2 receptor, the method comprising administering to a patient in need of such treatment a suitable amount of a compound of general formula (I) or (II).

In a further aspect of the invention, there is provided a novel compound of general formula (I) or (II) for use in medicine, particularly for use in the treatment or prevention of diseases and conditions mediated by $PGD_2$ at the CRTH2 receptor.

As mentioned above, such diseases and conditions include allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis and also other $PGD_2$-mediated diseases, for example autoimmune diseases such as hyper IgE syndrome and systemic lupus erythematosus, psoriasis, acne, multiple sclerosis, allograft rejection, reperfusion injury, chronic obstructive pulmonary disease, as well as rheumatoid arthritis, psoriatic arthritis and osteoarthritis.

The compounds of general formula (I) or (II) must be formulated in an appropriate manner depending upon the diseases or conditions they are required to treat.

Therefore, in a further aspect of the invention there is provided a pharmaceutical composition comprising a novel compound of general formula (I) or (II) together with a pharmaceutical excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a novel compound of general formula (I) or (II) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (II) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit $PGD_2$ at the CRTH2 receptor. The precise amount of a compound of general formula (I) or (II) which is therapeutically effective, and the route by which such compound is best administered, is readily determined by one of ordinary skill in the art by comparing the blood level of the agent to the concentration required to have a therapeutic effect.

Compounds of general formula (I) or (II) may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of a compound of general formula (I) or (II) in the preparation of an agent for the treatment of diseases and conditions mediated by $PGD_2$ at the CRTH2 receptor, wherein the agent also comprises an additional active agent useful for the treatment of the same diseases and conditions.

These additional active agents which may have a completely different mode of action include existing therapies for allergic and other inflammatory diseases including:

$\beta 2$ agonists such as salmeterol;

corticosteroids such as fluticasone;

antihistamines such as loratidine;

leukotriene antagonists such as montelukast;

anti-IgE antibody therapies such as omalizumab;

anti-infectives such as fusidic acid (particularly for the treatment of atopic dermatitis);

anti-fungals such as clotrimazole (particularly for the treatment of atopic dermatitis);

immunosuppressants such as tacrolimus and particularly pimecrolimus in the case of inflammatory skin disease.

CRTH2 antagonists may also be combined with therapies that are in development for inflammatory indications including:

other antagonists of $PGD_2$ acting at other receptors, such as DP antagonists;

inhibitors of phoshodiesterase type 4 such as cilonilast;

drugs that modulate cytokine production such as inhibitors of TNFα converting enzyme (TACE);

drugs that modulate the activity of Th2 cytokines IL-4 and IL-5 such as blocking monoclonal antibodies and soluble receptors;

PPAR-γ agonists such as rosiglitazone;

5-lipoxygenase inhibitors such as zileuton.

In yet a further aspect of the invention, there is provided a product comprising a novel compound of general formula (I) or (II) and one or more of the agents listed above as a combined preparation for simultaneous, separate or sequential use in the treatment of a disease or condition mediated by the action of $PGD_2$ at the CRTH2 receptor.

The invention will now be described in greater detail with reference to the following non limiting examples.

EXAMPLES

Example 1

Preparation of Compounds 1 to 19

1. {3-[1-(4-Chloro-phenyl)-ethyl]-5-fluoro-2-methyl-indol-1-yl}-acetic acid ethyl ester Triethylsilane (0.34 ml, 2.13 mmol) and trifluoroacetic acid (0.10 ml, 1.29 mmol) were sequentially added dropwise over 1 min to a stirred solution of (5-fluoro-2-methyl-indol-1-yl)-acetic acid ethyl ester (0.10 g, 0.43 mmol) and 4-acetylchlorobenzenze (64 mg, 0.41 mmol) in 1,2-dichloroethane (2 ml) at 0° C. The mixture was then warmed to room temperature and stirred for 16 h. The resulting mixture was concentrated in vacuo to leave a residue which was partitioned between ethyl acetate (10 ml) and a saturated solution of sodium bicarbonate (10 ml). The organic layer was separated, dried, and concentrated in vacuo to leave a residue which was purified by flash column chromatography (Flashmaster) on silica gel eluting with 10% ethyl acetate:heptane to 25% ethyl acetate:heptane to give the ethyl ester (57 mg, 37%) as a white solid, Tr=1.88 min (92%), m/z (ES$^+$) (M+H)$^+$374.30.

2. Compound 1—{3-[1-(4-Chloro-phenyl)-ethyl]-5-fluoro-2-methyl-indol-1-yl}-acetic acid Lithium hydroxide monohydrate (70 mg, 1.67 mmol) was added in one portion to a stirred solution of {3-[1-(4-chloro-phenyl)-ethyl]-5-fluoro-2-methyl-indol-1-yl}-acetic acid ethyl ester (57 mg, 0.15 mmol) in tetrahydrofuran : water (5 ml; 1:1) and stirred at room temperature for 2 h. The solution was adjusted to pH 1 with concentrated hydrochloric acid and the product extracted with ethyl acetate (3×10 ml). The combined organic extracts were dried and concentrated in vacuo to give the carboxylic acid (35 mg, 67%) as an off-white solid, $δ_H$ (400 MHz, CDCl$_3$) 7.26-7.21 (4H, m, Ar), 7.06 (1H, dd J 9.0, 4.2 Hz, Ar), 6.97 (1H, dd J 10.0, 2.4 Hz, Ar), 6.86 (1H, dt J 9.0, 2.4 Hz, Ar), 4.80 (2H, s, CH$_2$CO$_2$H), 4.35 (1H, q J 7.3 Hz, CHCH$_3$), 2.29 (3H, s, CH$_3$), 1.73 (3H, d J 7.3 Hz, CHCH$_3$); Tr=1.73 min (90%), m/z (ES$^+$) (M+H)$^+$346.09.

Compounds 2 to 19 were prepared using a similar method to that described for Compound 1, but with appropriately chosen starting materials.

Compound 2—{5-Fluoro-2-methyl-3-[1-(4-trifluoromethyl-phenyl)-ethyl]-indol-1-yl}-acetic acid $δ_H$ (400 MHz, CDCl$_3$) 7.50 (2H, d J 8.3 Hz, Ar), 7.39 (2H, d J 8.3 Hz, Ar), 7.07 (1H, dd J 8.8, 4.1 Hz, Ar), 6.98 (1H, dd J 10.0, 2.5 Hz, Ar), 6.85 (1H, dt J 9.0, 2.5 Hz, Ar), 4.80 (2H, s, CH$_2$CO$_2$H), 4.42 (1H, q J 7.1 Hz, CHCH$_3$), 2.29 (3H, s, CH$_3$), 1.77 (3H, d J 7.3 Hz, CHCH$_3$); Tr=1.65 min (96%), m/z (ES$^+$) (M+H)$^+$380.15.

Compound 3—{3-[1-(4-tert-Butyl-phenyl)-ethyl]-5-fluoro-2-methyl-indol-1-yl}-acetic acid $δ_H$ (400 MHz, CDCl$_3$) 7.32-7.21 (2H, m, Ar), 7.08-7.03 (2H, m, Ar), 6.89-6.83 (1H, m, Ar), 4.82 (2H, s, CH$_2$CO$_2$H), 4.36 (1H, q J 7.3 Hz, CHCH$_3$), 2.33 (3H, s, CH$_3$), 1.75 (3H, d J 7.3 Hz, CHCH$_3$), 1.29 (9H, s, C(CH$_3$)$_3$); Tr=1.78 min (97%), m/z (ES$^+$) (M+H)$^+$368.21.

Compound 4—{5-Fluoro-3-[1-(4-methanesulfonyl-phenyl)-ethyl]-2-methyl-indol-1-yl}-acetic acid $δ_H$ (400 MHz, CDCl$_3$) 7.81 (2H, d J 8.3 Hz, Ar), 7.47 (2H, d J 8.1 Hz, Ar), 7.06 (1H, dd J 8.8, 4.1Hz, Ar), 6.96 (1H, dd J 10.0, 2.5Hz, Ar), 6.85 (1H, dt J 9.0, 2.5Hz, Ar), 4.78 (2H, s, CH$_2$CO$_2$H), 4.43 (1H, q J 7.1 Hz, CHCH$_3$), 2.99 (3H, s, CH$_3$), 2.29 (3H, s, CH$_3$), 1.79 (3H, d J 7.3 Hz, CHCH$_3$); Tr=1.34 min (100%), m/z (ES$^+$) (M+H)$^+$390.16.

Compound 5—[5-Fluoro-2-methyl-3-(1-naphthalen-2-yl-ethyl)-indol-1-yl]-acetic acid $δ_H$ (400 MHz, CDCl$_3$) 7.81-7.74 (3H, m, Ar), 7.69 (1H, d J 8.5 Hz, Ar), 7.47-7.39 (2H, m, Ar), 7.39-7.33 (1H, m, Ar), 7.09-7.02 (2H, m, Ar), 6.86 (1H, dt J 9.0, 2.4 Hz, Ar), 4.83 (2H, s, CH$_2$CO$_2$H), 4.54 (1H, q J 7.3 Hz, CHCH$_3$), 2.32 (3H, s, CH$_3$), 1.86 (3H, d J 7.3 Hz, CHCH$_3$); Tr=1.66 min (97%), m/z (ES$^+$) (M+H)$^+$362.19.

Compound 6—(5-Fluoro-2-methyl-3-quinolin-2-ylmethyl-indol-1-yl)-acetic acid $δ_H$ (400 MHz, d$_6$-DMSO) 8.42 (1H, d J 9.0 Hz, Ar), 8.23 (1H, d J 9.0 Hz, Ar), 8.11 (1H, m, Ar), 7.97 (1H, m, Ar), 7.60 (1H, m, Ar) 7.51 (3H, m, Ar and Ar), 7.09 (1H, m, Ar), 5.19 (2H, s, CH$_2$), 4.56 (2H, CH$_2$), 2.63 (3H, s, CH$_3$); Tr=1.06 min (100%), m/z (ES$^+$) (M+H)$^+$349.35.

Compound 7—(5-Fluoro-2-methyl-3-naphthalen-2-ylmethyl-indol-1-yl)-acetic acid $δ_H$ (400 MHz, d$_6$-DMSO) 7.87 (4H, m, Ar), 7.47 (4H, m, Ar), 7.22 (1H, dd J 6.0, 1.5 Hz, Ar), 6.91 (1H, ddd J 9.0, 2.5 Hz, Ar), 5.04 (2H, s, CH$_2$), 4.23 (2H, s, CH$_2$), 2.42 (3H, s, CH$_3$); Tr=2.09 min, m/z (ES$^+$) (M+H)$^+$348.13.

Compound 8—[5-Fluoro-3-(8-hydroxy-quinolin-2-ylmethyl)-2-methyl-indol-1-yl]-acetic acid $δ_H$ (400 MHz, d$_6$-DMSO) 9.53 (1H, s, OH), 8.20 (1H, d J 8.0 Hz, Ar), 7.42 (5H, m, Ar), 7.13 (1H, dd J 6.0, 1.5 Hz, Ar), 6.91 (1H, dd J 9.0, 2.5 Hz, Ar), 5.00 (2H, s, CH$_2$), 4.41 (2H, s, CH$_2$), 2.47 (3H, s, CH$_3$); Tr=1.13 min, m/z (ES$^+$) (M+H)$^+$ 365.12.

Compound 9—(5-Fluoro-2-methyl-3-quinoxalin-2-ylmethyl-indol-1-yl)-acetic acid $δ_H$ (400 MHz d$_6$-DMSO) 9.02 (1H, s, H-3 Ar), 8.30 (2H, m, Ar), 8.05 (2H, m, Ar), 7.53 (2H, m, Ar), 7.07 (1H, m, Ar), 5.01 (2H, br s, CH$_2$), 4.64 (2H, s, CH$_2$), 2.64 (3H, s, CH$_3$); Tr=1.35 min, m/z (ES$^+$) (M+H)$^+$350.12.

Compound 10—[5-Fluoro-3-(4-methoxy-benzyl)-2-methyl-indol-1-yl]-acetic acid $δ_H$ (400 MHz, d$_6$-DMSO) 7.39 (1H, m, Ar), 7.16 (3H, m, Ar), 6.91 (3H, m, Ar) 5.00 (2H, s, CH$_2$), 3.98 (2H, s, CH$_2$), 3.74 (3H, s, OCH$_3$) 2.36 (3H, s, CH$_3$); Tr=1.93 min, m/z (ES$^+$) (M+H)$^+$328.13.

Compound 11—(5-Fluoro-2-methyl-3-thiazol-2-ylmethyl-indol-1-yl)-acetic acid ethyl ester Tr=1.09 min, m/z (ES$^+$) (M+H)$^+$305.26.

Compound 12—[3-(4-Chloro-benzyl)-5-fluoro-2-methyl-indol-1-yl]-acetic acid

Tr=1.63 min (100%), m/z (ES$^+$) (M+H)$^+$332.16.

Compound 13—(3-Benzothiazol-2-ylmethyl-5-fluoro-2-methyl-indol-1-yl)-acetic acid Tr=1.43 min, m/z (ES$^+$) (M+H)$^+$355.17.

Compound 14—[5-Fluoro-2-methyl-3-(4-trifluoromethyl-benzyl)-indol-1-yl]-acetic acid Tr=1.66 min, m/z (ES$^+$) (M+H)$^+$366.06.

Compound 15—[5-Fluoro-2-methyl-3-(4-tert-butyl-benzyl)-indol-1-yl]-acetic acid

Tr=1.73 min, m/z (ES$^+$) (M+H)$^+$354.21.

Compound 16—(3-Biphenyl4-ylmethyl-5-fluoro-2-methyl-indol-1-yl)-acetic acid

Tr'2.10 min, m/z (ES$^+$) (M+H)$^+$374.16.

Compound 17—[5-Fluoro-3-(4-methanesulfonyl-benzyl)-2-methyl-indol-1-yl]-acetic acid Tr=1.35 min, m/z (ES$^+$)=376.05.

Compound 18—[5-Fluoro-3-(6-fluoro-quinolin-2-ylmethyl)-2-methyl-indol-1-yl]-acetic acid $\delta_H$ (400 MHz, d$_6$-DMSO) 8.20 (1H, d J 8.6 Hz, Ar), 8.06 (1H, dd J 9.3, 5.6 Hz, Ar), 7.70 (1H, dd J 9.4, 2.8 Hz, Ar), 7.64 (1H, td J 8.8, 2.9 Hz, Ar), 7.37-7.32 (2H, m, Ar), 7.26 (1H, dd J 9.9, 2.6 Hz, Ar), 6.86 (1H, td J 9.2, 2.4 Hz, Ar), 4.94 (2H, s, CH$_2$), 4.33 (2H, s, CH$_2$), 2.40 (3H, s, CCH$_3$); Tr=1.28 min (100%), m/z (ES$^+$) (M+H)$^+$367.50.

Compound 19—(±)-3-(1-Benzothiazol-2-yl-ethyl)-5-fluoro-2-methyl-indol-1-yl]-acetic acid $\delta_H$ (400 MHz, d$_6$-DMSO) 8.01 (1H, d J 7.7 Hz, Ar), 7.95 (1H, d J 8.0 Hz, Ar), 7.49 (1H, obs t J 7.2 Hz, Ar), 7.43-7.36 (2H, m, Ar), 7.10 (1H, dd J 10.1, 2.5 Hz, Ar), 6.89 (1H, td J 9.2, 2.4 Hz, Ar), 5.01 (2H, s, CH$_2$), 4.91 (1H, q J 7.1 Hz, CHCH$_3$), 2.37 (3H, s, CCH$_3$), 1.87 (3H, d J 7.1 Hz, CHCH$_3$); Tr=1.53 min, m/z (ES$^+$) (M+H)$^+$369.10.

Compound 21—(2-Methyl-3-quinolin-2-ylmethyl-indol-1-yl)-acetic acid $\delta_H$ (400 MHz, d$_6$-DMSO) 8.16 (1H, d J 8.6 Hz, Ar), 8.01 (1H, d J 8.5 Hz, Ar), 7.88 (1H, d J 7.6 Hz, Ar), 7.74 (1H, t J 7.0 Hz, Ar), 7.54 (1H, t J 7.0 Hz, Ar), 7.44 (1H, d J 8.0 Hz, Ar), 7.26 (2H, app t J 8.9 Hz, Ar), 7.00 (1H, t J 7.3 Hz, Ar), 6.90 (1H, t J 7.3 Hz, Ar), 4.72 (2H, s, CH$_2$CO$_2$H), 4.35 (2H, s, CH$_2$), 2.40 (3H, s, CH$_3$); Tr=1.07 min (100%), m/z (ES$^+$) (M+H)$^+$331.33.

Compound 22—(5-Chloro-2-methyl-3-quinolin-2-ylmethyl-indol-1-yl)-acetic acid $\delta_H$ (400 MHz, d$_6$-DMSO) 8.21 (1H, d J 8.4 Hz, Ar), 8.00 (1H, d J 8.4 Hz, Ar), 7.89 (1H, d J 8.0 Hz, Ar), 7.77-7.73 (1H, m, Ar), 7.57-7.53 (2H, m, Ar), 7.40 (1H, d J 8.7 Hz, Ar), 7.29 (1H, d J 8.5 Hz, Ar), 7.04 (1H, dd J 8.6, 2.1 Hz, Ar), 5.00 (2H, s, CH$_2$CO$_2$H), 4.35 (2H, s, CH$_2$), 2.41 (3H, s, CH$_3$); Tr=1.17 min (95%), m/z (ES$^+$) (M+H)$^+$365.28.

Example 2

Preparation of Compound 20

1. [3-(4,5,7-Trifluoro-benzothiazol-2-ylmethyl)-indol-1-yl]-acetic acid ethyl ester This compound was prepared using the procedure set out in WO-A-0151489.

$\delta_H$ (400 MHz, d$_6$-DMSO) 7.75-7.69 (1H, m, Ar), 7.56 (1H, d J 7.8 Hz, Ar), 7.49 (1H, s, CH), 7.43 (1H, d J 8.2 Hz, Ar), 7.19 (1H, app t J 7.0 Hz, Ar), 7.08 (1H, app t J 7.1 Hz, Ar), 5.17 (2H, s, CH$_2$), 4.69 (2H, s, CH$_2$); 4.17 (2H, q J 7.2 Hz, CH$_2$CH$_3$), 1.23 (3H, t J 7.2 Hz, CH$_2$CH$_3$); Tr=1.62 min, m/z (ES$^+$) (M+H)$^+$405.15.

2. Compound 20—[3-(4,5,7-Trifluoro-benzothiazol-2-ylmethyl)-indol-1-yl]-acetic acid Lithium hydroxide (31 mg, 0.74 mmol) in water (6 ml) was added in one portion to a stirred solution of [3-(4,5,7-trifluoro-benzothiazol-2-ylmethyl)-indol-1-yl]-acetic acid ethyl ester (73 mg, 0.18 mmol) in tetrahydrofuran (6 ml) at room temperature. The mixture was stirred at room temperature for 15 min and then the solution was adjusted to pH ~3 with 1 M hydrochloric acid. The aqueous layer was then extracted with ethyl acetate (3×10 ml) and the combined organic extracts were washed with brine (10 ml), dried and concentrated in vacuo to give the carboxylic acid (62 mg, 92%) as a yellow solid, $\delta_H$ (400 MHz, d$_6$-DMSO) 7.76-7.69 (1H, m, Ar), 7.56 (1H, d J 8.0 Hz, Ar), 7.48 (1H, s, CH), 7.43 (1H, d J 8.3 Hz, Ar), 7.18 (1H, app t J 7.1 Hz, Ar), 7.07 (1H, app t J 7.1 Hz, Ar), 5.05 (2H, s, CH$_2$), 4.68 (2H, s, CH$_2$); Tr=1.94 min, m/z (ES$^+$) (M+H)$^+$377.00.

Example 3

Measurement of CRTH2 Antagonist Activity

Materials and Methods

Materials

Calcium-3 dye was purchased from Molecular Devices (Wokingham, UK). Mono-poly resolving medium was obtained from Dainippon Pharmaceuticals (Osaka, Japan). Macs anti-CD16 microbeads were from Miltenyi biotec (Bisley, Surrey). ChemoTx plates were purchased from Neuroprobe (Gaithesburg, Md.). Poly-D-lysine coated 96-well plates were obtained from Greiner (Gloucestershire, UK). [$^3$H]PGD$_2$ was from Amersham Biosciences (Buckinghamshire, UK). [$^3$H]SQ29548 was purchased from Perkin Elmer Life Sciences (Buckinghamshire, UK). All other reagents were obtained from Sigma-Aldrich (Dorset, UK), unless otherwise stated.

Methods

Cell Culture

Chinese Hamster Ovary cells were transfected with CRTH2 or DP receptors (CHO/CRTH2 and CHO/DP) and were maintained in culture in a humidified atmosphere at 37° C. (5% CO$_2$) in Minimum Essential Medium (MEM) supplemented with 10% foetal bovine serum, 2 mM glutamine, and 1 mg ml$^{-1}$ active G418. The cells were passaged every 2-3 days. For radioligand binding assay, cells were prepared in triple-layer flasks or in 175 cm$^2$ square flasks (for membrane preparation). For calcium mobilisation assay, cells were grown in a 96 well plate 24 h prior to the assay at a density of 80,000 cells per well.

Preparation of Cell Membranes

Membranes were prepared either from CHO/CRTH2 and CHO/DP cells, or from platelets (as a source of TP receptors). CHO cells grown to confluency were washed with PBS and detached using a Versene solution (15 ml per flask). When the cells were grown in 175 cm$^2$ square flask, they were collected by scrapping in PBS. The cell suspensions were centrifuged (1,700 rpm, 10 min, 4° C.) and resuspended in 15 ml of buffer (1×HBSS, supplemented with 10 mM HEPES, pH 7.3). Cell suspensions were then homogenised using an Ultra Turrax at setting 4-6 for 20 s. The homogenate was centrifuged at 1,700 rpm for 10 min and the supernatant was collected and centrifuged at 20,000 rpm for 1 h at 4° C. The resulting pellet was resuspended in buffer and stored at −80° C. in aliquots of 200-500 µl. The protein concentration was determined by the method of Bradford (1976), using bovine serum albumin as standard. The platelets were washed by centrifugation at 600×g for 10 min and resuspended in ice-cold assay buffer (10 mM Tris-HCl, pH 7.4, 5 mM Glucose, 120 mM NaCl, 10 µM indomethacin) and directly centrifuged at 20,000 rpm for. 30 min at 4° C. The resulting pellet was treated as described above.

Radioligand Binding Assays

[$^3$H]PGD$_2$ (160 Ci/mmol) binding experiments were performed on membranes prepared as described above. Assays were performed in a final volume of 100 µl of buffer (1×HBSS/HEPES 10 mM, pH 7.3). Cell membranes (15 µg). Cell membranes 15 mg were preincubated at room temperature with varying concentration of competing ligand for 15 min. [$^3$H]PGD$_2$ (mol, final concentration) was then added and the incubation continued for a further one hour at room temperature. The reaction was terminated by the addition of 200

µl ice-cold assay buffer to each well, followed by rapid filtration through Whatman GF/B glass fibre filters using a Unifilter Cell harvester (PerkinElmer Life Sciences) and six washes of 300 µl of ice-cold buffer. The Unifilter plates were dried at room temperature for at least 1 h and the radioactivity retained on the filters was determined on a Beta Trilux counter (PerkinElmer Life Sciences), following addition of 40 µl of Optiphase Hi-Safe 3 (Wallac) liquid scintillation. Non specific binding was defined in the presence of 10 µM unlabelled PGD$_2$. Assays were performed in duplicate.

The results of the radioligand binding experiments to the CRTH2 and DP receptors are shown in Tables 1 and 2.

TABLE 1

Radioligand binding data (Ki on CRTH2 Receptor).

| Compounds | Ki (nM) |
|---|---|
| Compound 4 | 5 ± 4 |
| Compound 6 | 9 ± 3 |
| Compound 8 | 6 ± 4 |
| Compound 12 | 11 ± 2 |
| Compound 13 | 6 ± 1 |
| Compound 17 | 7 ± 2 |
| Compound 18 | 1.3 ± 0.6 |
| Compound 20 (lidorestat) | 886 ± 248 |

TABLE 2

Radioligand binding data (Ki on DP Receptor).

| Compounds | Ki(nM) |
|---|---|
| Compound 4 | 30440 ± 9805 |
| Compound 6 | 17870 ± 7290 |
| Compound 8 | 7710 ± 1780 |
| Compound 12 | 12220 ± 2250 |
| Compound 18 | 7740 ± 1442 |
| Compound 20 (lidorestat) | 3960 |

The TP receptor radioligand binding was done on membranes prepared from platelets. 15-40 µg of protein were pre-incubated with varying concentrations of competing ligand for 15 min at room temperature in assay buffer (10 mM Tris-HCl, pH 7.4, 5 mM glucose, 120 mM NaCl, 10 µM indomethacin). [$^3$H]SQ29548 (38 Ci/mmol, 10 nM final concentration) was then added and the incubation continued for a further 30 min at room temperature. The reaction was terminated by the addition of 200 µl ice-cold assay buffer to each well, followed by rapid filtration through Whatman GF/C glass fibre filters using a Unifilter Cell harvester (PerkinElmer Life Sciences) followed with six washes of 300 µl of ice-cold buffer. The radioactivity was determined as described above.

All of the compounds studied in this assay bound to the TP receptor with low affinity (Ki>1 µM).

Compounds of general formula (I) bound to CRTH2 receptor expressed in CHO cells with a range of affinity varying from very high to moderate. In fact the Ki values determined in competition versus [$^3$H]PGD$_2$ varied from 500 pM to 1 µM. Compounds of general formula (I) had no activity (or very weak activity) at the DP and TP receptors. The binding selectivity of the compounds of general formula (I) for CRTH2 receptor was greater than 200 fold for CRTH2 receptor, compared to DP and TP receptors.

Calcium Mobilisation Assay

Cells were seeded onto poly-D-lysine coated 96-well plates at a density of 80,000 cells per well and incubated at 37° C. overnight to allow the cells to adhere. Cells were washed twice with HBSS and incubated for 1 h at 37° C. in 100 µl HBSS and 100 µl calcium-3-dye (Molecular Devices), supplemented with 4 mM probenecid. Changes in fluorescence were monitored over a 50 s time course with agonist addition at 17 s using a Flexstation (Molecular Devices).

Effect of CRTH2 Agonists on Calcium Mobilisation in CHO-CRTH2 Cells

PGD$_2$ caused a dose-dependent increase in intracellular Ca$^{2+}$ mobilisation in CHO/CRTH2 cells, with an EC$_{50}$=2.4±0.5 nM (n=3).

Effect of Compounds of General Formula (I) on the Calcium Mobilisation Induced by PGD$_2$ PGD$_2$-stimulated Ca$^{2+}$ flux was fully inhibited by the compounds of general formula (I) and the IC$_{50}$ value for each compound in the calcium assay was comparable to its Ki value in Radioligand binding. IC$_{50}$ values of compounds of general formula (I) varied from 5 nM to 1 µM. The results for several compounds of general formula (I) are shown in Table 3. Increasing doses of the compounds of general formula (I) caused a dose-dependent and parallel shift of the PGD$_2$ dose response curve in CHO/CRTH2 cells, thereby indicating that the compounds are competitive CRTH2 antagonists.

The antagonistic effect of the compounds of general formula (I) appears to be CRTH2 selective, since no inhibitory effect was seen with ATP-stimulated Ca$^{2+}$ flux.

TABLE 3

Inhibition of PGD$_2$-induced calcium flux

| Compounds | IC$_{50}$ (nM) |
|---|---|
| Compound 4 | 55 ± 18 |
| Compound 6 | 30 ± 6 |
| Compound 7 | 38 ± 16 |
| Compound 8 | 11 ± 6 |
| Compound 10 | 47 ± 8 |
| Compound 12 | 108 ± 29 |
| Compound 17 | 64 ± 5 |
| Compound 18 | 10 ± 5 |
| Compound 19 | 34 ± 7 |
| Compound 20 (lidorestat) | 885 ± 96 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for the treatment of a disease selected from the group consisting of allergic asthma, perennial allergic rhinitis, seasonal allergic rhinitis, atopic dermatitis, contact hypersensitivity, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematosus, acne, multiple sclerosis, allograft rejection, chronic obstructive pulmonary disease, rheumatoid arthritis, psoriatic arthritis and osteoarthritis, comprising administering to a patient in need of such treatment an effective amount of a compound of general formula (I):

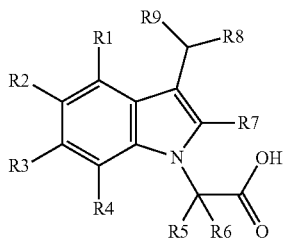

wherein
R¹, R³ and R⁴ are hydrogen;
R² is halo;
R⁵ and R⁶ are hydrogen;
R⁷ is $C_1$-$C_6$ alkyl;
R⁸ is a phenyl, naphthalenyl, thiazole, biphenyl, quinolinyl or quinoxalinyl group, any of which may be substituted with one or more halo, $C_1$-$C_6$ alkyl, —O($C_1$-$C_6$)alkyl, —$SO_2R^{11}$, or —OH groups;
wherein $R^{11}$ is independently hydrogen or $C_1$-$C_6$ alkyl;
R⁹ is hydrogen;
or a pharmaceutically acceptable salt thereof.

2. The method of claim 1, wherein, in the compound of general formula (I), R² is fluoro; and R⁷ is methyl.

3. The method of claim 1 wherein the compound of general formula (I) is selected from the group consisting of:
{3-[1-(4-Chloro-phenyl)-ethyl]-5-fluoro-2-methyl-indol-1-yl)}-acetic acid,
{5-Fluoro-2-methyl-3-[1-(4-trifluoromethyl-phenyl)-ethyl]indol-1-yl)}-acetic acid,
{3-[1-(4-tert-Butyl-phenyl)-ethyl]-5-fluoro-2-methyl-indol-1-yl}-acetic acid,
{5-Fluoro-3-[1-(4-methanesulfonyl-phenyl)-ethyl]-2-methyl-indol-1-yl}-acetic acid,
[5-Fluoro-2-methyl-3-(1-naphthalen-2-yl-ethyl)-indol-1-yl]-acetic acid,
(5-Fluoro-2-methyl-3-quinolin-2-ylmethyl-indol-1-yl)-acetic acid,
(5-Fluoro-2-methyl-3-naphthalen-2-ylmethyl-indol-1-yl)-acetic acid,
[5-Fluoro-3-(8-hydroxy-quinolin-2-ylmethyl)-2-methyl-indol-1-yl]-acetic acid,
(5-Fluoro-2-methyl-3-quinoxalin-2-ylmethyl-indol-1-yl)-acetic acid,
[5-Fluoro-3-(4-methoxy-benzyl)-2-methyl-indol-1-yl]-acetic acid,
(5-Fluoro-2-methyl-3-thiazol-2-ylmethyl-indol-1-yl)-acetic acid ethyl ester,
[3-(4-Chloro-benzyl)-5-fluoro-2-methyl-indol-1-yl]-acetic acid,
[5-Fluoro-2-methyl-3-(4-trifluoromethyl-benzyl)-indol-1-yl]-acetic acid,
[5-Fluoro-2-methyl-3-(4-tert-butyl-benzyl)-indol-1-yl]-acetic acid,
(3-Biphenyl-4-ylmethyl-5-fluoro-2-methyl-indol-1-yl)-acetic acid,
[5-Fluoro-3-(4-methanesulfonyl-benzyl)-2-methyl-indol-1-yl]-acetic acid,
[5-Fluoro-3-(6-fluoro-quinolin-2-ylmethyl)-2-methyl-indol-1-yl]-acetic acid, and
(5-Chloro-2-methyl-3-quinolin-2-ylmethyl-indol-1-yl)-acetic acid.

4. The method of claim 1 wherein the compound of general formula (I) is (5-Fluoro-2-methyl-3-quinolin-2-ylmethyl-indol-1-yl)-acetic acid.

5. The method of claim 1, wherein the disease is selected from the group consisting of allergic asthma, allergic rhinitis, perennial allergic rhinitis, seasonal allergic rhinitis, atopic dermatitis, allergic conjunctivitis, eosinophilic bronchitis, and chronic obstructive pulmonary disease.

6. The method of claim 1, wherein the disease is allergic asthma.

7. The method of claim 1, wherein the disease is allergic rhinitis.

8. The method of claim 1, wherein the disease is chronic obstructive pulmonary disease.

9. The method of claim 1, further comprising administering one or more additional active agents selected from the group consisting of β2agonists, corticosteroids, antihistamines, leukotriene antagonists, anti-IgE antibody therapies, anti-infectives, anti-fungals, immunosuppressants, other agonists of $PGD_2$ acting at other receptors such as DP antagonists, inhibitors of phosphodiesterase type 4, drugs that modulate cytokine production, drugs that modulate the activity of Th2 cytokines IL-4 and IL-5, PPAR-γ agonists, and 5-lipoxygenase inhibitors.

10. The method of claim 9, wherein the additional active agent is a leukotriene antagonist which is montelukast.

11. A method for the treatment of a disease selected from the group consisting of allergic asthma, perennial allergic rhinitis, seasonal allergic rhinitis, atopic dermatitis, contact hypersensitivity, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematosus, acne, multiple sclerosis, allograft rejection, chronic obstructive pulmonary disease, rheumatoid arthritis, psoriatic arthritis, and osteoarthritis, comprising administering to a patient in need of such treatment an effective amount of a pharmaceutical composition comprising a pharmaceutical excipient or carrier and a compound of general formula (I):

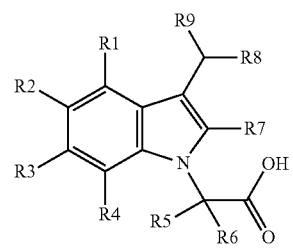

wherein
R¹, R³ and R⁴ are hydrogen;
R² is halo;
R⁵ and R⁶ are hydrogen;
R⁷ is $C_1$-$C_6$ alkyl;
R⁸ is a phenyl, naphthalenyl, thiazole, biphenyl, quinolinyl or quinoxalinyl group, any of which may be substituted with one or more halo, $C_1$-$C_6$ alkyl, —O($C_1$-$C_6$)alkyl, —$SO_2R^{11}$, or —OH groups;
wherein $R^{11}$ is independently hydrogen or $C_1$-$C_6$ alkyl; and
R⁹ is hydrogen;
or a pharmaceutically acceptable salt thereof.

12. The method of claim 11, wherein R² is fluoro.

13. The method of claim 11, wherein the compound of general formula (I) is selected from the group consisting of:
- {3-[1-(4-Chloro-phenyl)-ethyl]-5-fluoro-2-methyl-indol-1-yl}-acetic acid,
- {5-Fluoro-2-methyl-3-[1-(4-trifluoromethyl-phenyl)-ethyl]-indol-1-yl}-acetic acid,
- {3-[1-(4-tert-Butyl-phenyl)-ethyl]-5-fluoro-2-methyl-indol-1-yl}-acetic acid,
- {5-Fluoro-3-[1-(4-methanesulfonyl-phenyl)-ethyl]-2-methyl-indol-1-yl}-acetic acid,
- [5-Fluoro-2-methyl-3-(1-naphthalen-2-yl-ethyl)-indol-1-yl]-acetic acid,
- (5-Fluoro-2-methyl-3-quinolin-2-ylmethyl-indol-1-yl)-acetic acid,
- (5-Fluoro-2-methyl-3-naphthalen-2-ylmethyl-indol-1-yl)-acetic acid,
- [5-Fluoro-3-(8-hydroxy-quinolin-2-ylmethyl)-2-methyl-indol-1-yl]-acetic acid,
- (5-Fluoro-2-methyl-3-quinoxalin-2-ylmethyl-indol-1-yl)-acetic acid,
- [5-Fluoro-3-(4-methoxy-benzyl)-2-methyl-indol-1-yl]-acetic acid,
- (5-Fluoro-2-methyl-3-thiazol-2-ylmethyl-indol-1-yl)-acetic acid ethyl ester,
- [3-(4-Chloro-benzyl)-5-fluoro-2-methyl-indol-1-yl]-acetic acid,
- [5-Fluoro-2-methyl-3-(4-trifluoromethyl-benzyl)-indol-1-yl]-acetic acid,
- [5-Fluoro-2-methyl-3-(4-tert-butyl-benzyl)-indol-1-yl]-acetic acid,
- (3-Biphenyl-4-ylmethyl-5-fluoro-2-methyl-indol-1-yl)-acetic acid,
- [5-Fluoro-3-(4-methanesulfonyl-benzyl)-2-methyl-indol-1-yl]-acetic acid,
- [5-Fluoro-3-(6-fluoro-quinolin-2-ylmethyl)-2-methyl-indol-1-yl]-acetic acid, and
- (5-Chloro-2-methyl-3-quinolin-2-ylmethyl-indol-1-yl)-acetic acid.

14. The method of claim 11, wherein the compound of general formula (I) is (5-Fluoro-2-methyl-3-quinolin-2-ylmethyl-indol-1-yl)-acetic acid.

15. The method of claim 11, wherein the composition is formulated for oral, rectal, nasal, bronchial, topical, vaginal, or parenteral administration.

16. The method of claim 11, wherein the composition is formulated for oral administration.

17. The method of claim 11, wherein the pharmaceutical carrier is selected from the group consisting of syrup, acacia, gelatin, sorbitol, tragacanth, polyvinylpyrrolidone, methylcellulose, ethylcellulose, sodium carboxy nethylcellulose, hydroxypropylmethylcellulose, sucrose, starch, corn starch, gelatin, lactose, sucrose, microcrystalline cellulose, kaolin, mannitol, dicalcium phosphate, sodium chloride, alginic acid, magnesium stearate, sodium stearate, metallic stearates, glycerol stearate, stearic acid, silicone fluid, talc waxes, oils, and colloidal silica.

* * * * *